United States Patent [19]
Peter et al.

[11] Patent Number: 6,117,214
[45] Date of Patent: Sep. 12, 2000

[54] WATER TRAP FOR A SAMPLE GAS FLOW

[75] Inventors: Gerd Peter; Thomas Maxeiner, both of Lübeck, Germany

[73] Assignee: Dräger Medizintechnik GmbH, Lübeck, Germany

[21] Appl. No.: 09/287,149

[22] Filed: Apr. 6, 1999

[30] Foreign Application Priority Data

Jan. 16, 1999 [DE] Germany .......................... 199 01 590

[51] Int. Cl.$^7$ .................................................. B01D 19/00
[52] U.S. Cl. ..................................... 96/6; 96/157; 96/192
[58] Field of Search .............................. 95/46; 96/6, 157, 96/168, 169, 174, 192

[56] References Cited

U.S. PATENT DOCUMENTS

| | | | |
|---|---|---|---|
| 4,529,419 | 7/1985 | Perl et al. | 96/6 |
| 4,853,013 | 8/1989 | Rio et al. | 96/6 |
| 4,886,528 | 12/1989 | Aaltonen et al. | 55/158 |
| 4,990,054 | 2/1991 | Janocko | 96/6 X |
| 5,749,942 | 5/1998 | Mattis et al. | 95/46 |

*Primary Examiner*—Robert H. Spitzer
*Attorney, Agent, or Firm*—McGlew and Tuttle, P.C.

[57] ABSTRACT

A water trap for a sample gas flow includes a housing 1 fastened to a holder 2. The housing 1 has a tank 3 for receiving liquids and gases. Above the tank 3, the housing 1 contains a first chamber divided by a first hydrophobic membrane 10. The lower divided part 12 of the first chamber is connected to the sample gas flow via the holder 2 on the inlet side and to the gas space in the tank 3 on the outlet side. The upper divided part 11 of the first chamber is connected to a gas analyzer 4 via the holder 2 and is connected to a vacuum. The housing 1 contains a second chamber divided by a second hydrophobic membrane 20. The lower divided part 22 of the second chamber is connected to the gas space in the tank 3 at a point 18 which is located lower in the direction of the liquid level and relative to the entry of the connection line from the first chamber. The upper divided part 21 of the second chamber is connected to a volume flow meter 8 and to the same vacuum. The free areas through which the gas flows and the pore sizes of the first and second hydrophobic membranes are selected so that the ratio of the gas volume flow through the first and second hydrophobic membranes is in the range of 5:1 to 20:1.

13 Claims, 2 Drawing Sheets

WATER TRAP FOR A SAMPLE GAS FLOW

FIELD OF THE INVENTION

The present invention pertains to a water trap for a sample gas flow from a sample gas line.

BACKGROUND OF THE INVENTION

It is desirable, especially in the case of patients connected to anesthesia apparatuses or respirators, to measure the concentration of individual gases or of a plurality of gases in the breathing gas flow by means of suitable gas analyzers. It has been known that condensed water from breathing gas drawn off by means of vacuum is collected in water traps to protect such gas analyzers and also to prevent possible errors in measurement.

To recognize and guarantee the ability of such water traps to function, it would be advantageous if the operating state and the degree of filling of the tank receiving the separated water were displayed.

The prior-art water traps do not meet either the desired requirements in terms of accuracy and they do not permit more than two different operating states to be recognized, and they generate false alarms because of the principle of display used and/or are impractical in handling.

A prior-art water trap is described in U.S. Pat. No. 4,886,528, in which no specific filling level recognition is provided. With the tank filled, the gas flow resistance increases greatly, so that no more gas can pass through the water trap, i.e., only two operating states, namely, able to function and unable to function, can be recognized.

SUMMARY AND OBJECTS OF THE INVENTION

The primary object of the present invention is to propose a water trap for a sample gas flow from a sample gas line, which permits improved handling with improved accuracy of display of a plurality of different operating states at the same time and avoids the drawbacks of the prior-art water traps.

According to the invention, a water trap for a sample gas flow from a sample gas line is provided. The water trap includes a housing, which is detachably fastened to a holder. The housing has a tank for receiving liquids and gases. Above the tank the housing contains a first chamber divided by a first hydrophobic membrane. A lower divided part of the first chamber is connected to a sample gas line via the holder on an inlet side and to a gas space in the tank on the outlet side. The upper divided part of the first chamber is connected above the first hydrophobic membrane to a gas analyzer via the holder and is connected downstream to a vacuum. Above the tank, the housing contains a second chamber divided by means of a second hydrophobic membrane. The lower divided part of the second chamber is connected to the gas space in the tank at a point which is located lower relative to the liquid level and relative to the entry of the connection line from the first chamber, and wherein the upper divided part of the second chamber is connected above the second hydrophobic membrane via the holder to a volume flow meter and to the same vacuum. The free areas through which the gas volume flow flows and the pore sizes of the first and second hydrophobic membranes are selected to be such that the ratio of the gas volume flow through the first hydrophobic membrane to the gas volume flow through the second hydrophobic membrane is in the range of 5:1 to 20:1, and especially about 10:1.

The outlet from the housing may be connected to an inner line extending in the direction of the bottom of the tank, so that the liquids in the tank can be emptied by means of an external vacuum applied, especially by means of a syringe.

The pore sizes of the first and second hydrophobic membranes may be smaller than about 0.45 $\mu$m. The hydrophobic membrane may have a free area of 95 to 110 mm$^2$ through which the gas volume flow flows, with a pore size of about 0.2 $\mu$m, and the second hydrophobic membrane may have a free area of 15 to 30 mm$^2$ through which the gas volume flow flows, with a pore size of about 0.1 $\mu$m.

The pump for generating the vacuum may be arranged downstream of the gas analyzer in the direction of gas flow. The gas line led over the volume flow meter may open into the connection line between the gas analyzer and the pump.

An evaluating and control unit and a total volume flow meter are preferably arranged downstream of the pump. The measured signals of the volume flow meter and the total volume flow meter are sent to the evaluating and control unit, so that they are compared with stored threshold values for the volume flow and total volume flow and the current operating state of the water trap is displayed as a function of this comparison. The total volume flow may be regulated to a constant value by means of the pump.

The essential advantages of the water trap according to the present invention are that, due to its design, reliable operation is guaranteed even in the case of a large amount of water generated in the sample gas flow, improved display of different operating states is possible, the handling, especially the emptying of the tank, is improved, and no additional restrictions (flow resistance) for splitting the gas volume flows is needed, and the water trap is less susceptible to disturbances and can be integrated more simply within the measuring set-up as a result, and bacteria and microorganisms are retained more reliably at the same time.

One exemplary embodiment of the present invention will be explained below on the basis of the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
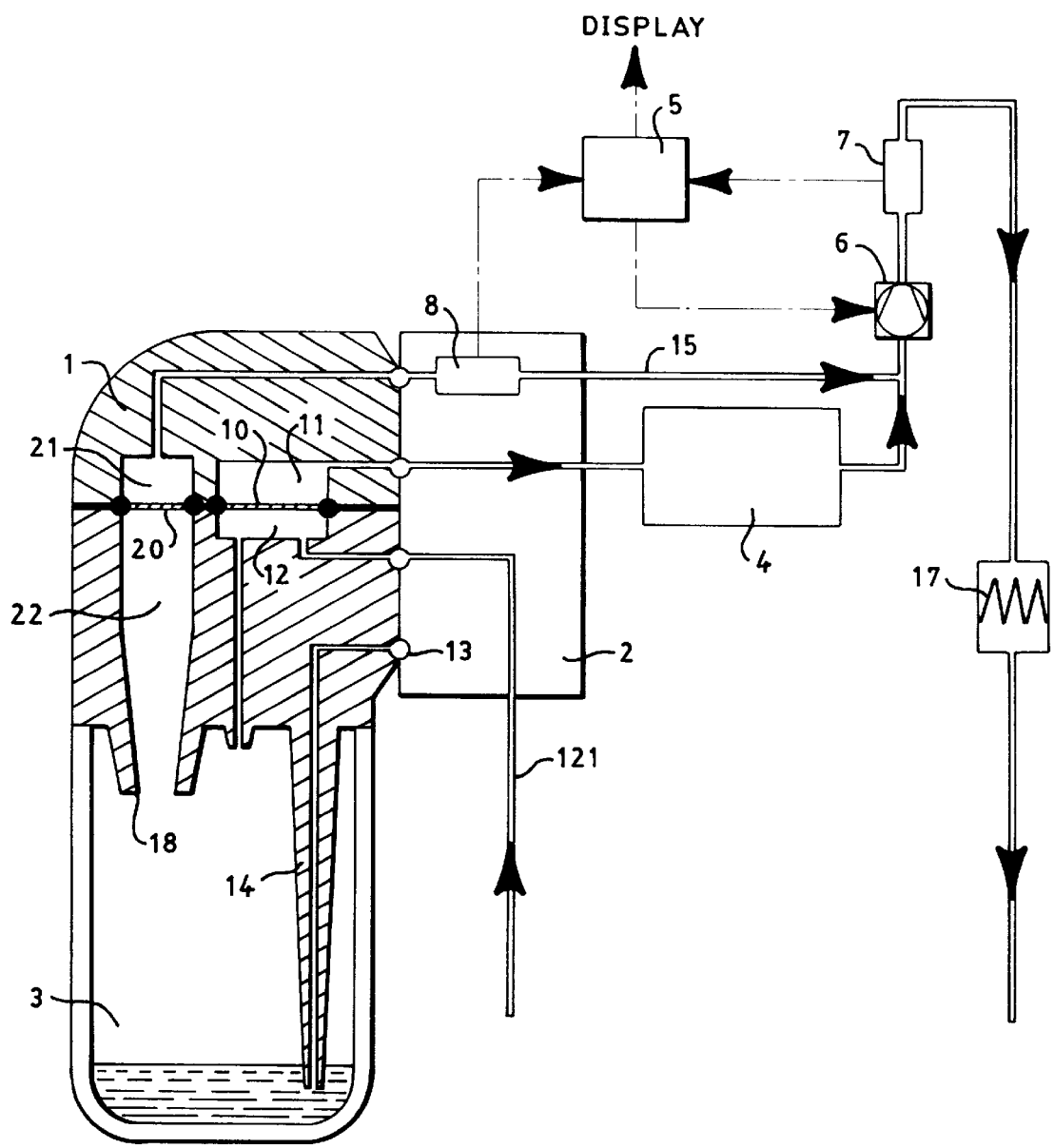
FIG. 1 is a schematic view showing an arrangement according to the present invention.

Referring to the drawings in particular, the water trap according to the present invention according to FIG. 1 has as an essential principal component a housing 1, which is detachably fastened to the holder 2 by means of suitable connections. The tank 3 for receiving liquids, especially water, and gases, which is preferably transparent and is rigidly connected to the housing, is located under the housing 1. Above the tank 3, the housing 1 contains a first chamber, which is divided by means of a first hydrophobic membrane 10, wherein the lower, divided part 12 of the first chamber is connected on the inlet side via the holder 2 to the sample gas line 121 to the breathing gas flow and the outlet side to the gas space in the tank 3, and wherein the upper, divided part 11 of the first chamber is connected above the first hydrophobic membrane 10 via the holder 2 to at least one, preferably infrared optical and/or electrochemical gas analyzer 4 and to a vacuum (pump 6). Above the tank 3, the housing 1 contains a second chamber divided by means of a second hydrophobic membrane 20, wherein the lower divided part 22 of this second chamber is connected to the gas space in the tank 3 at a point 18 which is lower relative to the liquid level and relative to the entry of the connection line from the first chamber. In addition, the upper divided part 21 of the second chamber is connected to a volume flow meter 8 and to the vacuum (pump 6) above the second hydrophobic membrane 20 via the holder 2 and line 15. A thermal mass flow meter operating according to the heat transfer principle, which has a high sensitivity of measurement even at low volume flows, on the one hand, and has a simple design and is therefore inexpensive, on the other hand, is used as an especially preferred volume flow meter 8.

The free areas through which the gas volume flow, i.e., the sample gas flow, flows and the pore sizes of the first and second hydrophobic membranes 10, 20, which preferably consist of GORETEX®, are selected to be such that the ratio of the gas volume flow through the first hydrophobic membrane 10 to the gas volume flow through the second hydrophobic membrane 20 is in the range of 5:1 to 20:1 and is especially about 10:1, wherein the pore sizes of the two membranes 10, 20 are smaller than about 0.45 $\mu$m. The pore sizes of the two membranes 10, 20 are preferably in the range of about 0.1 to 0.2 $\mu$m, so that bacteria and microorganisms are reliably retained by the membranes 10, 20.

The water trap preferably has an outlet 13 from the housing 1, which outlet is connected to an inner line 14, which nearly reaches the bottom of the tank 3, so that the liquids in the tank 3 can be emptied by means of an external vacuum applied conveniently and hygienically, especially by means of a usual syringe with a suitable, standardized connection. Furthermore, the water trap according to the exemplary embodiment is provided with an evaluating and control unit 5 and with a total volume flow meter 7 downstream of the pump 6, so that the measured signals of the volume and total volume flow meters 8, 7 are sent to the evaluating and control unit 5 and are compared with stored threshold values for the volume and total volume flows there, and the current operating state of the water trap is subsequently displayed as a function of this comparison of the values.

The total volume flow is regulated to a constant value within a preset range by means of the evaluating and control unit 5 and the pump 6. By means of the gas volume flow-measuring means, namely, the volume flow meter 8 and the total volume flow meter 7, it is possible to provide detailed information on the operating state of the water trap and to display it by means of the evaluating and control unit 5. Thus, it is possible, e.g., to trigger an alarm when the liquid level in the tank 3 has reached a certain upper limit. This happens when the gas volume flow measured by means of the volume flow meter 8 through the second divided chamber drops below the preset, stored gas volume flow value that corresponds to the normal operating state, as soon as the liquid level reaches the line from the tank 3 into the second chamber at point 18.

In contrast to the state of the art, it is consequently possible to recognize not only whether the water trap is able to function or not, but the following additional operating states can be recognized as well: "Water trap is drawn off," "first hydrophobic membrane 10 is clogged" or "draw-off section of water trap, sample gas line 121 is clogged."

The total gas volume flow is split according to the present invention between the first and second divided chambers by designing the free areas and the pore sizes of the first and second hydrophobic membranes 10, 20 in the water trap and without additional external flow resistances for the total volume flow.

This is particularly advantageous because in the case of a large amount of water generated in the breathing gas flow to be analyzed, water, which would lead to failure of the water trap, is efficiently prevented from accumulating in the first chamber. This is made possible by the special routing of the gas and the design of the hydrophobic membrane material, which increases the gas volume flow through the second hydrophobic membrane 20 when the differential pressure over the second hydrophobic membrane 20, which is generated by the pump 6, increases in the case of a large amount of water generated. The gas volume flow through the second chamber increases superproportionally in this case and there is increased drainage from the first chamber. A far poorer drainage effect is obtained in the case of the use of external flow resistances to split the total gas volume flow in prior-art water traps, because the dynamic resistance of external flow resistances increases with increasing gas volume flow and it limits the gas volume flow needed for the drainage of the first chamber far more greatly than in the case of the design according to the present invention. Another advantage of the present invention according to the exemplary embodiment is the possibility of emptying the liquid from the tank 3 hygienically by means of a connection provided especially for this purpose at the outlet 13 and by means of a commercially available disposable syringe.

A filter 17, which is used to collect particles separated by the device, is optionally located in an outgoing gas line behind the gas volume flow meter 7, which is designed, e.g., as a pressure pick-up above a flow resistance.

Figure 2A:
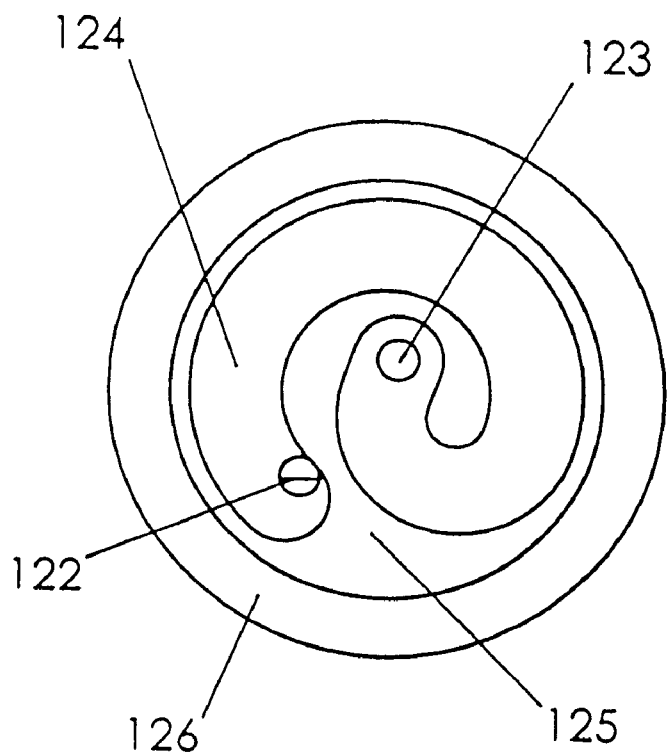
FIG. 2A is a top view of the lower divided part of the first chamber.
Figure 2B:
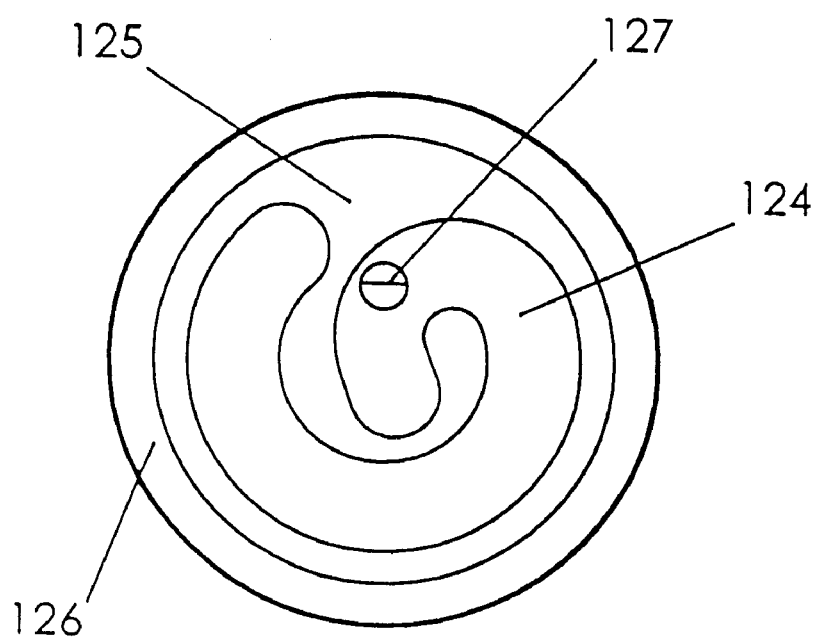
FIG. 2B is a top view of the upper divided part of the first chamber.

In the top part of the page, FIG. 2 shows a top view of the lower part 12 of the first chamber of the housing 1, which is preferably manufactured from a plastic according to the injection molding process. The lower part of the page shows a top view of the upper, divided part 11 of the first chamber of the housing 1, which housing is likewise made of a plastic according to the injection molding process.

The hole 122 leads to the sample gas line 121, the hole 123 to the tank 3, and the hole 127 leads to the gas analyzer 4 via a line. The sealing groove 126 is used to sealingly receive the first hydrophobic membrane 10 enclosed by means of a ring-shaped, elastic seal.

The flow profile 125, which is complementary at top and bottom, is elevated relative to the flat flow channel 124, so that the sample gas flow sweeps over the largest possible area of the membrane 10 because of the resulting gas routing, on the one hand, and, on the other hand, condensed liquid or water drops are transported highly effectively in the lower part 12 of the first chamber to the hole 123 and thus to the tank 3. As a result, it is achieved through an arrangement and design according to the present invention as shown in the exemplary embodiment that a relatively large percentage of the sample gas flow reaches the gas analyzer 4 and the liquid is effectively separated in the water trap.

While a specific embodiment of the invention has been shown and described in detail to illustrate the application of the principles of the invention, it will be understood that the invention may be embodied otherwise without departing from such principles.

What is claimed is:

1. A water trap for a sample gas flow from a sample gas line, the water trap comprising:

a holder;

a gas analyzer;

a vacuum;

a volume flow meter;

a water trap housing detachably fastened to said holder, said housing having a tank for receiving liquids and gases, above said tank, said housing having a first chamber divided by means of a first hydrophobic membrane into a first chamber lower divided part and a first chamber upper divided part, wherein said first chamber lower divided part is connected to the sample gas line via said holder on an inlet side and to the gas space in said tank on the outlet side, and wherein said first chamber upper divided part is connected above said first hydrophobic membrane to said gas analyzer via said holder and is connected downstream to said vacuum, above said tank, said housing having a second chamber divided by means of a second hydrophobic membrane into a second chamber lower divided part and a second chamber upper divided part, said second chamber lower divided part being connected to the gas space in said tank at a point which is located lower relative to the liquid level and relative to the entry of the connection line from said first chamber, and wherein said second chamber upper divided part is connected above said second hydrophobic membrane via said holder to said volume flow meter and to said vacuum, free areas being defined through which the gas volume flow flows, said free areas and pore sizes of said first and second hydrophobic membranes being selected to be such that a ratio of the gas volume flow through said first hydrophobic membrane to the gas volume flow through said second hydrophobic membrane being in a range of 5:1 to 20:1.

2. The water trap in accordance with claim 1, wherein said ratio is about 10:1.

3. The water trap in accordance with claim 2, wherein an outlet from said housing is connected to an inner line extending in a direction of the bottom of said tank, so that liquids in said tank can be emptied by means of an external vacuum applied.

4. The water trap in accordance with claim 3, wherein said external vacuum is applied by a syringe.

5. Water trap in accordance with claim 2, wherein the pore sizes of said first and second hydrophobic membranes are smaller than about 0.45 $\mu$m.

6. The water trap in accordance with claim 1, wherein an outlet from said housing is connected to an inner line extending in a direction of the bottom of said tank, so that liquids in said tank can be emptied by means of an external vacuum applied.

7. The water trap in accordance with claim 6, wherein said external vacuum is applied by a syringe.

8. Water trap in accordance with claim 6, wherein the pore sizes of said first and second hydrophobic membranes are smaller than about 0.45 $\mu$m.

9. Water trap in accordance with claim 1, wherein the pore sizes of said first and second hydrophobic membranes are smaller than about 0.45 $\mu$m.

10. The water trap in accordance with claim 1, wherein said first hydrophobic membrane has a free area of 95 to 110 mm$^2$ through which the gas volume flow flows, with a pore size of about 0.2 $\mu$m, and said second hydrophobic membrane has a free area of 15 to 30 mm$^2$ through which the gas volume flow flows, with a pore size of about 0.1 $\mu$m.

11. The water trap in accordance with claim 1, wherein said vacuum includes a pump for generating the vacuum, said pump being arranged downstream of said gas analyzer in the direction of gas flow, and a gas line is led over said volume flow meter and opens into a connection line between said gas analyzer and said pump.

12. The water trap in accordance with claim 11, further comprising an evaluating and control unit and a total volume flow meter arranged downstream of said pump, wherein measured signals of said volume flow meter and said total volume flow meter are sent to said evaluating and control unit, they are compared with stored threshold values for the volume flow and total volume flow and the current operating state of the water trap is displayed as a function of this comparison.

13. The water trap in accordance with claim 12, wherein said total volume flow is regulated to a constant value by means of said pump.

* * * * *